US012778875B2

(12) United States Patent
Morvan et al.

(10) Patent No.: US 12,778,875 B2
(45) Date of Patent: Nov. 3, 2026

(54) COSMETIC COMPOSITION COMPRISING A CATIONIC ASSOCIATIVE POLYMER, A CARBOXYLIC ANIONIC SURFACTANT, OPTIONALLY A NONIONIC SURFACTANT AND AN AMPHOTERIC OR ZWITTERIONIC SURFACTANT

(71) Applicant: L'Oreal, Paris (FR)

(72) Inventors: Christelle Morvan, Saint Ouen (FR); Andreia Teixeira, Saint Ouen (FR); Estelle Mathonneau, Saint Ouen (FR)

(73) Assignee: L'Oreal, Paris (FR)

( * ) Notice: Subject to any disclaimer, the term of this patent is extended or adjusted under 35 U.S.C. 154(b) by 794 days.

(21) Appl. No.: 17/758,059

(22) PCT Filed: Dec. 16, 2020

(86) PCT No.: PCT/EP2020/086561
§ 371 (c)(1),
(2) Date: Jun. 27, 2022

(87) PCT Pub. No.: WO2021/122840
PCT Pub. Date: Jun. 24, 2021

(65) Prior Publication Data

US 2023/0050392 A1 Feb. 16, 2023

(30) Foreign Application Priority Data

Dec. 18, 2019 (FR) ...................................... 1914769

(51) Int. Cl.

*A61K 8/73* (2006.01)
*A61K 8/42* (2006.01)
*A61K 8/44* (2006.01)
*A61K 8/891* (2006.01)
*A61Q 5/12* (2006.01)

(52) U.S. Cl.

CPC ................ *A61K 8/731* (2013.01); *A61K 8/42* (2013.01); *A61K 8/44* (2013.01); *A61K 8/891* (2013.01); *A61Q 5/12* (2013.01); *A61K 2800/5426* (2013.01); *A61K 2800/548* (2013.01)

(58) Field of Classification Search

CPC ...................................................... A61K 8/731
See application file for complete search history.

(56) References Cited

U.S. PATENT DOCUMENTS

| | | | | |
|---|---|---|---|---|
| 2011/0158927 A1* | 6/2011 | Viravau | A61K 8/463 | 424/70.13 |
| 2011/0200664 A1* | 8/2011 | Ebinger | A61K 8/732 | 424/731 |
| 2017/0027832 A1* | 2/2017 | Wang | A61K 8/8147 | |

FOREIGN PATENT DOCUMENTS

| | | | |
|---|---|---|---|
| EP | 2 343 042 B1 | 7/2011 | |
| WO | 2017/207270 A1 | 12/2017 | |
| WO | WO-2017207685 A1 * | 12/2017 | A61K 8/39 |
| WO | 2018/108919 A1 | 6/2018 | |
| WO | 2018/109148 A1 | 6/2018 | |
| WO | WO 2020/001984 | 1/2020 | |
| WO | WO 2020/002103 | 1/2020 | |
| WO | WO 2020/002107 | 1/2020 | |
| WO | WO 2021/121859 | 6/2021 | |
| WO | WO 2021/122840 | 6/2021 | |

OTHER PUBLICATIONS

R.T. Jones and C.A. Brown. "The behaviour of cationic cellulose derivatives containing fatty quat groups." International Journal of Cosmetic Science, vol. 10, 1988, pp. 219-229. (Year: 1988).*

ICI Americas Inc. "The HLB System a time-saving guide to emulsifier selection." ICI Americas Inc. Wilmington, Delaware, Revised Mar. 1980, pp. 1-22. (Year: 1980).*

KW Herrmann. "Micellar Properties of Some Zwitterionic Surfactants." Journal of Colloid and Interface Science, vol. 22, 1966, pp. 352-359. (Year: 1966).*

Hans Schott. "Effect of Chain Length in Homologous Series of Anionic Surfactants on Irritant Action and Toxicity." Journal of Pharmaceutical Sciences, vol. 62, No. 2, Feb. 1973, pp. 341-343. (Year: 1973).*

M. Jayne Lawrence et al. "Aggregation and Surface Properties of Synthetic Double-chain Non-ionic Surfactants in Aqueous Solution." Journal of Pharmacy and Pharmacology, vol. 49, 1997, pp. 594-600. (Year: 1997).*

International Search Report and Written Opinion as mailed on Mar. 17, 2021, issued in corresponding International Application No. PCT/EP2020/086561, filed Dec. 16, 2020, 8 pages.

* cited by examiner

*Primary Examiner* — Isaac Shomer
(74) *Attorney, Agent, or Firm* — CHRISTENSEN O'CONNOR JOHNSON KINDNESS PLLC

(57) ABSTRACT

The invention relates to a cosmetic composition comprising a cationic associative polymer, a particular carboxylic anionic surfactant, optionally a nonionic surfactant and an amphoteric or zwitterionic surfactant. The invention also relates to a cosmetic process for treating keratin fibres, in particular human keratin fibres such as the hair, comprising the application of said cosmetic composition. The invention also relates to the use of said cosmetic composition for conditioning keratin fibres, in particular human keratin fibres such as the hair.

15 Claims, No Drawings

COSMETIC COMPOSITION COMPRISING A CATIONIC ASSOCIATIVE POLYMER, A CARBOXYLIC ANIONIC SURFACTANT, OPTIONALLY A NONIONIC SURFACTANT AND AN AMPHOTERIC OR ZWITTERIONIC SURFACTANT

The invention relates to a cosmetic composition comprising a cationic associative polymer, a particular carboxylic anionic surfactant, optionally a nonionic surfactant and an amphoteric or zwitterionic surfactant.

The invention also relates to a cosmetic process for treating keratin fibres, in particular human keratin fibres such as the hair, comprising the application of said cosmetic composition.

The invention also relates to the use of said cosmetic composition for conditioning keratin fibres, in particular human keratin fibres such as the hair.

Hair is generally damaged and embrittled by the action of external atmospheric agents such as light and bad weather, and also by mechanical or chemical treatments, such as brushing, combing, dyeing, bleaching, permanent-waving and/or relaxing, or even repeated washing.

Hair is thus damaged by these various factors and may over time become dry, coarse, brittle or dull, notably in fragile areas, and more particularly at the ends.

Thus, to overcome these drawbacks, it is common practice to resort to haircare treatments using compositions that condition the hair, giving it satisfactory cosmetic properties, notably in terms of smoothness, sheen, softness, suppleness, lightness, a natural feel and good disentangling properties.

These haircare compositions intended to be applied regularly to the hair may be, for example, hair conditioners, masks or sera, and may be in the form of gels, hair lotions or care creams that are more or less thick.

The products present on the market generally have a thick texture and are difficult to apply and to spread over the entire head of hair. The user thus finds these products rather unpleasant to use.

Now, users are in search of haircare products that are easy to apply and pleasant to use, while at the same time affording good sensory and care properties to the keratin fibres.

It has been discovered, surprisingly, that a cosmetic composition comprising at least one cationic associative polymer, at least one particular carboxylic anionic surfactant, optionally at least one nonionic surfactant, at least one amphoteric surfactant, and optionally at least one silicone makes it possible to achieve the objectives presented above.

Specifically, the composition according to the invention affords care that is advantageously transparent, and has good working qualities, such as a pleasant texture and a foaming aspect. The composition is also easy to spread over all the keratin fibres and is highly rinseable.

The composition according to the invention gives keratin fibres good cosmetic properties, such as a homogeneous soft, smooth feel, suppleness and good coating. The keratin fibres are also easy to disentangle and are not made heavy by the composition.

One subject of the invention is thus a cosmetic composition comprising:

a) one or more cationic associative polymers, b) one or more alkyl(amido)ether carboxylic anionic surfactants, c) optionally one or more nonionic surfactants, d) one or more amphoteric or zwitterionic surfactants, and e) optionally one or more silicones.

A subject of the present invention is also a cosmetic process for treating keratin fibres, in particular human keratin fibres such as the hair, comprising the application to said keratin fibres of a composition as defined above.

A subject of the invention is also the use of the cosmetic composition as defined above, for conditioning keratin fibres, in particular human keratin fibres such as the hair.

Other subjects, characteristics, aspects and advantages of the invention will emerge even more clearly on reading the description and the examples that follow.

In the text hereinbelow, unless otherwise indicated, the limits of a range of values are included in that range, notably in the expressions "between" and "ranging from . . . to . . . ".

The expression "at least one" used in the present description is equivalent to the expression "one or more".

a) Cationic Associative Polymers

The cosmetic composition according to the invention comprises one or more cationic associative polymers a).

It is recalled that "associative polymers" are polymers that are capable, in an aqueous medium, of reversibly associating with each other or with other molecules.

Their chemical structure more particularly comprises at least one hydrophilic zone and at least one hydrophobic zone.

The term "hydrophobic group" means a radical or polymer with a saturated or unsaturated, linear or branched hydrocarbon-based chain, comprising at least 8 carbon atoms, preferably from 8 to 30 carbon atoms, in particular from 12 to 30 carbon atoms and more preferentially from 18 to 30 carbon atoms.

Preferentially, the hydrocarbon-based group is derived from a monofunctional compound. By way of example, the hydrophobic group may be derived from a fatty alcohol such as stearyl alcohol, dodecyl alcohol or decyl alcohol. It may also denote a hydrocarbon-based polymer, for instance polybutadiene.

Among the associative cationic polymers that may be used, mention may be made, alone or as a mixture, of:

(A) cationic associative polyurethanes, which may be represented by the general formula (Ia) below:

$$R\text{-}X\text{-}(P)_n\text{-}[L\text{-}(Y)_m]_r\text{-}L'\text{-}(V)_p\text{-}X'\text{-}R'$$

in which:

R and R', which may be identical or different, represent a hydrophobic group or a hydrogen atom;

X and X', which may be identical or different, represent a group including an amine function optionally bearing a hydrophobic group, or alternatively a group L";

L, L' and L", which may be identical or different, represent a group derived from a diisocyanate;

P and P', which may be identical or different, represent a group including an amine function optionally bearing a hydrophobic group;

Y represents a hydrophilic group;

r is an integer between 1 and 100 inclusive, preferably between 1 and 50 inclusive and in particular between 1 and 25 inclusive;

n, m and p are each, independently of each other, between 0 and 1000 inclusive;

the molecule containing at least one protonated or quaternized amine function and at least one hydrophobic group.

Preferably, the only hydrophobic groups are the groups R and R' at the chain ends.

One preferred family of cationic associative polyurethanes is the one corresponding to formula (Ia) described above, in which:

R and R' both independently represent a hydrophobic group,

X and X' each represent a group L", n and p are integers that are between 1 and 1000 inclusive, and L, L', L", P, P', Y and m have the meaning indicated above.

Another preferred family of cationic associative polyurethanes is the one corresponding to formula (Ia) above in which:

n=p=0 (the polymers do not include any units derived from a monomer containing an amine function, incorporated into the polymer during the polycondensation), the protonated amine functions result from the hydrolysis of excess isocyanate functions, at the chain end, followed by alkylation of the primary amine functions formed with alkylating agents containing a hydrophobic group, i.e. compounds of the type RQ or R'Q, in which R and R' are as defined above and Q denotes a leaving group such as a halide or a sulfate.

Yet another preferred family of cationic associative polyurethanes is the one corresponding to formula (Ia) above in which:

R and R' both independently represent a hydrophobic group,

X and X' both independently represent a group including a quaternary amine, n=p=0, and L, L', Y and m have the meaning given above.

The number-average molecular mass (Mn) of the cationic associative polyurethanes is preferably between 400 and 500000 inclusive, in particular between 1000 and 400000 inclusive and ideally between 1000 and 300000 inclusive.

The term "hydrophobic group" means a radical or polymer containing a saturated or unsaturated, linear or branched hydrocarbon-based chain, which may contain one or more heteroatoms such as P, O, N or S, or a radical containing a perfluoro or silicone chain. When the hydrophobic group denotes a hydrocarbon-based radical, it includes at least 10 carbon atoms, preferably from 10 to 30 carbon atoms, in particular from 12 to 30 carbon atoms and more preferentially from 18 to 30 carbon atoms.

Preferentially, the hydrocarbon-based group is derived from a monofunctional compound.

By way of example, the hydrophobic group may be derived from a fatty alcohol such as stearyl alcohol, dodecyl alcohol or decyl alcohol. It may also denote a hydrocarbon-based polymer, for instance polybutadiene.

When X and/or X' denote(s) a group including a tertiary or quaternary amine, X and/or X' may represent one of the following formulae:

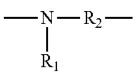
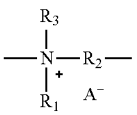
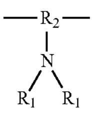
or

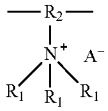
for X

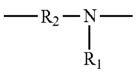
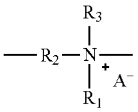
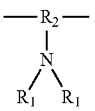
or

-continued

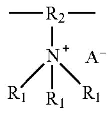
for X' in which:

$R_2$ represents a linear or branched alkylene radical containing from 1 to 20 carbon atoms, optionally including a saturated or unsaturated ring, or an arylene radical, one or more of the carbon atoms possibly being replaced with a heteroatom chosen from N, S, O and P;

$R_1$ and $R_3$, which may be identical or different, denote a linear or branched C1-C30 alkyl or alkenyl radical or an aryl radical, at least one of the carbon atoms possibly being replaced with a heteroatom chosen from N, S, O and P;

$A^-$ is a physiologically acceptable anionic counterion such as a halide, for instance chloride or bromide, or mesylate.

The groups L, L' and L" represent a group of formula:

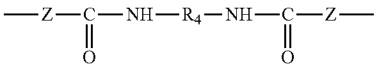

in which:

Z represents —O—, —S— or —NH—; and $R_4$ represents a linear or branched alkylene radical containing from 1 to 20 carbon atoms, optionally including a saturated or unsaturated ring, or an arylene radical, one or more of the carbon atoms possibly being replaced with a heteroatom chosen from N, S, O and P.

The groups P and P' comprising an amine function may represent at least one of the following formulae:

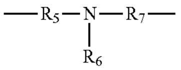
or
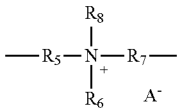
or

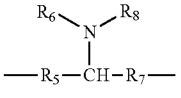
or
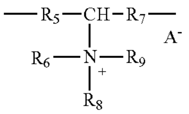
or

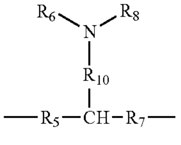
or
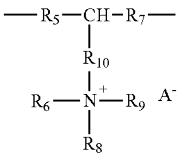

in which:

$R_5$ and $R_7$ have the same meanings as $R_2$ defined previously;

$R_6$, $R_8$ and $R_9$ have the same meanings as $R_1$ and $R_3$ defined previously;

$R_{10}$ represents a linear or branched, optionally unsaturated alkylene group possibly containing one or more heteroatoms chosen from N, O, S and P; and $A^-$ is a physiologically acceptable anionic counterion such as a halide, for instance chloride or bromide, or mesylate.

As regards the meaning of Y, the term "hydrophilic group" means a polymeric or non-polymeric water-soluble group.

By way of example, when it is not a polymer, mention may be made of ethylene glycol, diethylene glycol and propylene glycol.

When it is a hydrophilic polymer, in accordance with one preferred embodiment, mention may be made, for example, of polyethers, sulfonated polyesters, sulfonated polyamides or a mixture of these polymers. The hydrophilic compound is preferentially a polyether and notably a poly(ethylene oxide) or poly(propylene oxide).

The cationic associative polyurethanes of formula (Ia) according to the invention are formed from diisocyanates and from various compounds bearing functions containing labile hydrogen. The functions containing labile hydrogen may be alcohol, primary or secondary amine or thiol functions, giving, after reaction with the diisocyanate functions, polyurethanes, polyureas and polythioureas, respectively. In the present invention, the term "polyurethanes" encompasses these three types of polymer, namely polyurethanes per se, polyureas and polythioureas, and also copolymers thereof.

A first type of compound involved in the preparation of the polyurethane of formula (Ia) is a compound including at least one unit bearing an amine function. This compound may be multifunctional, but the compound is preferentially difunctional, that is to say that, according to a preferential embodiment, this compound includes two labile hydrogen atoms borne, for example, by a hydroxyl, primary amine, secondary amine or thiol function. A mixture of multifunctional and difunctional compounds in which the percentage of multifunctional compounds is low may also be used.

As mentioned above, this compound may include more than one unit containing an amine function. In this case, it is a polymer bearing a repetition of the unit containing an amine function.

Compounds of this type may be represented by one of the following formulae:

$$HZ—(P)_n—ZH \text{ or } HZ—(P')_p—ZH,$$

in which Z, P, P', n and p are as defined above.

Examples that may be mentioned include N-methyldiethanolamine, N-tert-butyldiethanolamine and N-sulfoethyldiethanolamine.

The second compound included in the preparation of the polyurethane of formula (Ia) is a diisocyanate corresponding to the formula:

$$O=C=N—R_4—N=C=O$$

in which $R_4$ is as defined above.

By way of example, mention may be made of methylenediphenyl diisocyanate, methylenecyclohexane diisocyanate, isophorone diisocyanate, tolylene diisocyanate, naphthalene diisocyanate, butane diisocyanate and hexane diisocyanate.

A third compound involved in the preparation of the polyurethane of formula (Ia) is a hydrophobic compound intended to form the terminal hydrophobic groups of the polymer of formula (Ia).

This compound is formed form a hydrophobic group and a function containing a labile hydrogen, for example a hydroxyl, primary or secondary amine, or thiol function.

By way of example, this compound may be a fatty alcohol such as stearyl alcohol, dodecyl alcohol or decyl alcohol. When this compound includes a polymeric chain, it may be, for example, α-hydroxylated hydrogenated polybutadiene.

The hydrophobic group of the polyurethane of formula (Ia) may also result from the quaternization reaction of the tertiary amine of the compound including at least one tertiary amine unit. Thus, the hydrophobic group is introduced via the quaternizing agent. This quaternizing agent is a compound of the type RQ or R'Q, in which R and R' are as defined above and Q denotes a leaving group such as a halide, a sulfate, etc.

The cationic associative polyurethane may also comprise a hydrophilic block. This block is provided by a fourth type of compound involved in the preparation of the polymer. This compound may be multifunctional. It is preferably difunctional. It is also possible to have a mixture in which the percentage of multifunctional compound is low.

The functions containing labile hydrogen are alcohol, primary or secondary amine or thiol functions. This compound may be a polymer terminated at the chain ends with one of these functions containing labile hydrogen.

By way of example, when it is not a polymer, mention may be made of ethylene glycol, diethylene glycol and propylene glycol.

When it is a hydrophilic polymer, mention may be made, for example, of polyethers, sulfonated polyesters and sulfonated polyamides, or a mixture of these polymers. The hydrophilic compound is preferentially a polyether and notably a poly(ethylene oxide) or poly(propylene oxide).

The hydrophilic group termed Y in formula (Ia) is optional. Specifically, the units containing a quaternary or protonated amine function may suffice to provide the solubility or water-dispersibility required for this type of polymer in an aqueous solution.

Although the presence of a hydrophilic group Y is optional, cationic associative polyurethanes including such a group are, however, preferred.

(B) quaternized cellulose derivatives, and in particular quaternized celluloses modified with groups including at least one fatty chain, such as linear or branched alkyl groups, linear or branched arylalkyl groups, or linear or branched alkylaryl groups, preferably linear or branched alkyl groups, these groups including at least 8 carbon atoms, notably from 8 to 30 carbon atoms, better still from 10 to 24, or even from 10 to 14, carbon atoms; or mixtures thereof.

Preferably, mention may be made of quaternized hydroxyethylcelluloses modified with groups including at least one fatty chain, such as linear or branched alkyl groups, linear or branched arylalkyl groups, or linear or branched alkylaryl groups, preferably linear or branched alkyl groups, these groups including at least 8 carbon atoms, notably from 8 to 30 carbon atoms, better still from 10 to 24, or even from 10 to 14, carbon atoms; or mixtures thereof.

Preferentially, mention may be made of the hydroxyethylcelluloses of formula (Ib):

(Ib)

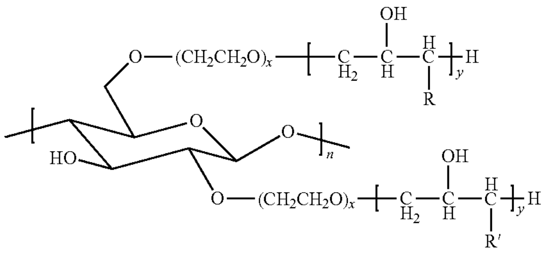

in which:

R represents an ammonium group $R_aR_bR_cN^+$, $Q^-$ in which $R_a$, $R_b$ and $R_c$, which may be identical or different, represent a hydrogen atom or a linear or branched $C_1$-$C_{30}$ alkyl, and $Q^-$ represents an anionic counterion such as a halide, for instance a chloride or bromide; preferably an alkyl;

R' represents an ammonium group $W'_aR'_bR'_cN^+$—, $Q'^-$ in which $R'_a$, $R'_b$ and $R'_c$, which may be identical or different, represent a hydrogen atom or a linear or branched $C_1$-$C_{30}$ alkyl, and $Q'^-$ represents an anionic counterion such as a halide, for instance a chloride or bromide; preferably an alkyl;

it being understood that at least one of the radicals $R_a$, $R_b$, $R_c$, $R'_a$, $R'_b$ and $R'_c$ represents a linear or branched $C_8$-$C_{30}$ alkyl;

n, x and y, which may be identical or different, represent an integer between 1 and 10000.

Preferably, in formula (Ib), at least one of the radicals $R_a$, $R_b$, $R_c$, $R'_a$, $R'_b$ or $R'_c$ represents a linear or branched $C_8$-$C_{30}$, better still $C_{10}$-$C_{24}$ or even $C_{10}$-$C_{14}$ alkyl; mention may be made in particular of the dodecyl radical ($C_{12}$). Preferably, the other radical(s) represent a linear or branched $C_1$-$C_4$ alkyl, notably methyl.

Preferably, in formula (Ib), only one of the radicals $R_a$, $R_b$, $R_c$, $R'_a$, $R'_b$ or $R'_c$ represents a linear or branched $C_8$-$C_{30}$, better still $C_{10}$-$C_{24}$ or even $C_{10}$-$C_{14}$ alkyl; mention may be made in particular of the dodecyl radical (Cu). Preferably, the other radicals represent a linear or branched $C_1$-$C_4$ alkyl, notably methyl.

Even better still, R may be a group chosen from —$N^+(CH_3)_3$, $Q'^-$ and —$N^+(C_{12}H_{25})(CH_3)_2$, $Q'^-$, preferably an —$N^+(CH_3)_3$, $Q'^-$ group.

Even better still, R' may be a group —$N^+(C_{12}H_{25})(CH_3)_2$, $Q'^-$.

The aryl radicals preferably denote phenyl, benzyl, naphthyl or anthryl groups.

Mention may notably made of the polymers having the following INCI names:

- Polyquaternium-24, such as the product Quatrisoft LM 200®, sold by the company Amerchol/Dow Chemical;
- PG-Hydroxyethylcellulose Cocodimonium Chloride, such as the product Crodacel QM®;
- PG-Hydroxyethylcellulose Lauryldimonium Chloride ($C_{12}$ alkyl), such as the product Crodacel QL®; and
- PG-Hydroxyethylcellulose Stearyldimonium Chloride ($C_{18}$ alkyl), such as the product Crodacel QS®, sold by the company Croda.

Mention may also be made of the hydroxyethylcelluloses of formula (Ib) in which R represents a trimethylammonium halide and R' represents a dimethyldodecylammonium halide, preferentially R represents trimethylammonium chloride $(CH_3)_3N^+$—, $Cl^-$ and R' represents dimethyldodecylammonium chloride $(CH_3)_2(C_{12}H_{25})N^+$—, $Cl^-$. This type of polymer is known under the INCI name Polyquaternium-67; as commercial products, mention may be made of the Softcat Polymer SL® polymers, such as SL-100, SL-60, SL-30 and SL-5, from the company Amerchol/Dow Chemical.

More particularly, the polymers of formula (Ib) are, for example, those whose viscosity is between 2000 and 3000 cPs inclusive, preferentially between 2700 and 2800 cPs. Typically, Softcat Polymer SL-5 has a viscosity of 2500 cPs, Softcat Polymer SL-30 has a viscosity of 2700 cPs, Softcat Polymer SL-60 has a viscosity of 2700 cPs and Softcat Polymer SL-100 has a viscosity of 2800 cPs. Use may also be made of Softcat Polymer SX-1300X with a viscosity of between 1000 and 2000 cPs [cf. Internet info]

(C) cationic polyvinyllactams, notably those comprising:

a) at least one monomer of vinyllactam or alkylvinyllactam type;

b) at least one monomer of structure (Ic) or (IIc) below:

(Ic)

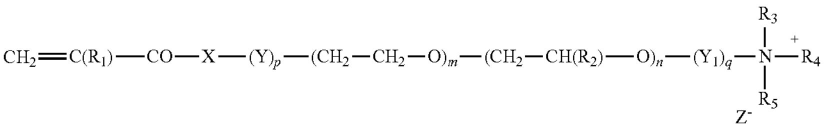

(IIc)

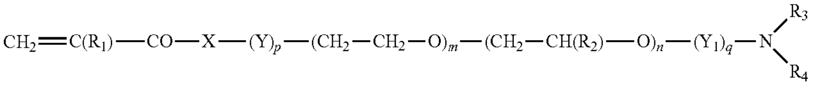

in which:

X denotes an oxygen atom or a radical $NR_6$, $R_1$ and $R_6$ denote, independently of each other, a hydrogen atom or a linear or branched $C_1$-$C_5$ alkyl radical, $R_2$ denotes a linear or branched $C_1$-$C_4$ alkyl radical, $R_3$, $R_4$ and $R_5$ denote, independently of each other, a hydrogen atom, a linear or branched $C_1$-$C_{30}$ alkyl radical or a radical of formula (IIIc):

$$—(Y_2)_r—(CH_2—CH(R_7)—O)_x—R_8 \quad \text{(IIIc)}$$

Y, $Y_1$ and $Y_2$ denote, independently of each other, a linear or branched $C_2$-$C_{16}$ alkylene radical, $R_7$ denotes a hydrogen atom or a linear or branched $C_1$-$C_4$ alkyl radical or a linear or branched $C_1$-$C_4$ hydroxyalkyl radical, $R_8$ denotes a hydrogen atom or a linear or branched $C_1$-$C_{30}$ alkyl radical, p, q and r denote, independently of each other, 0 or 1, m and n denote, independently of each other, an integer ranging from 0 to 100 inclusive, x denotes an integer ranging from 1 to 100 inclusive, Z denotes an anionic counterion of an organic or mineral acid, such as a halide, for instance chloride or bromide, or mesylate;

with the proviso that:

at least one of the substituents $R_3$, $R_4$, $R_5$ or $R_8$ denotes a linear or branched $C_8$-$C_{30}$ alkyl radical, if m and/or n is other than zero, then q is equal to 1, if m=n=0, then p or q is equal to 0.

The cationic poly(vinyllactam) polymers according to the invention may be crosslinked or non-crosslinked and may also be block polymers.

Preferably, the counterion $Z^-$ of the monomers of formula (Ic) is chosen from halide ions, phosphate ions, the methosulfate ion and the tosylate ion.

Preferably, $R_3$, $R_4$ and $R_5$ denote, independently of each other, a hydrogen atom or a linear or branched $C_1$-$C_{30}$ alkyl radical.

More preferentially, the monomer b) is a monomer of formula (Ic) for which, preferentially, m and n are equal to 0.

The vinyllactam or alkylvinyllactam monomer is preferably a compound of structure (IVc):

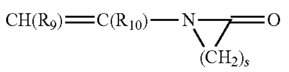

(IVc)

in which:

s denotes an integer ranging from 3 to 6, $R_9$ denotes a hydrogen atom or a linear or branched $C_1$-$C_5$ alkyl radical, $R_{10}$ denotes a hydrogen atom or a linear or branched $C_1$-$C_5$ alkyl radical, with the proviso that at least one of the radicals $R_9$ and $R_{10}$ denotes a hydrogen atom.

Even more preferentially, the monomer (IVc) is vinylpyrrolidone.

The cationic poly(vinyllactam) polymers according to the invention may also contain one or more additional monomers, preferably cationic or nonionic monomers.

As compounds that are particularly preferred, mention may be made of the following terpolymers comprising at least:

a) one monomer of formula (IVc), b) one monomer of formula (Ic) in which p=1, m=n=q=0, $R_3$ and $R_4$ denote, independently of each other, a hydrogen atom or a $C_1$-$C_5$ alkyl radical and $R_5$ denotes a linear or branched $C_8$-$C_{24}$ alkyl radical, and c) one monomer of formula (IIc) in which p=1, m=n=q=0, $R_3$ and $R_4$ denote, independently of each other, a hydrogen atom or a linear or branched $C_1$-$C_5$ alkyl radical.

Even more preferentially, terpolymers comprising, by weight, 40% to 95% of monomer (a), 0.1% to 55% of monomer (c) and 0.25% to 50% of monomer (b) will be used. Such polymers are notably described in patent application WO-00/68282.

As cationic polymer(vinyllactam) polymers according to the invention, the following are notably used:

vinylpyrrolidone/dimethylaminopropylmethacrylamide/dodecyldimethylmethacrylamidopropylammonium tosylate terpolymers, vinylpyrrolidone/dimethylaminopropylmethacrylamide/cocoyldimethylmethacrylamidopropylammonium tosylate terpolymers, vinylpyrrolidone/dimethylaminopropylmethacrylamide/lauryldimethylmethacrylamidopropylammonium tosylate or chloride terpolymers.

The vinylpyrrolidone/dimethylaminopropylmethacrylamide/lauryldimethylmethylacrylamidopropylammonium chloride terpolymer is notably sold by the company ISP under the names Styleze W10® and Styleze W20L® (INCI name: Polyquaternium-55).

The weight-average molecular mass (Mw) of the cationic poly(vinyllactam) polymers is preferably between 500 and 20000000, more particularly between 200000 and 2000000 and preferentially between 400000 and 800000.

(D) the cationic polymer(s) obtained by polymerization of a monomer mixture comprising one or more vinyl monomers substituted with one or more amino groups, one or more hydrophobic nonionic vinyl monomers, and one or more associative vinyl monomers, as described in patent application WO 2004/024779.

Among these copolymers, mention may be made more particularly of the products of polymerization of a monomer mixture comprising:

a di($C_1$-$C_4$ alkyl)amino($C_1$-$C_6$ alkyl) methacrylate, one or more $C_1$-$C_{30}$ alkyl esters of (meth)acrylic acid, a polyethoxylated $C_{10}$-$C_{30}$ alkyl methacrylate (20-25 mol of ethylene oxide units), a 30/5 polyethylene glycol/polypropylene glycol allyl ether, a hydroxy($C_2$-$C_6$ alkyl) methacrylate, and an ethylene glycol dimethacrylate.

Such a polymer is, for example, the compound sold by the company Lubrizol under the name Carbopol Aqua CC® and which corresponds to the INCI name Polyacrylate-1 Crosspolymer.

Advantageously, the cationic associative polymer(s) a) are chosen from quaternized (poly)hydroxyethylcelluloses modified with groups including at least one fatty chain, such as alkyl, arylalkyl or alkylaryl groups including at least 10 carbon atoms, or mixtures thereof.

Preferably, the cationic associative polymer(s) a) are chosen from quaternized (poly)hydroxyethylcelluloses modified with groups including at least one alkyl group containing at least 10 carbon atoms, preferentially ranging from 10 to 22 carbon atoms, and more preferentially ranging from 12 to 16 carbon atoms.

More preferentially, the cationic associative polymer a) is an associative cationic polymer having the INCI name Polyquaternium-67.

Advantageously, the total content of the cationic associative polymer(s) a) ranges from 0.01% to 10% by weight, preferably from 0.05% to 5% by weight, more preferentially from 0.1% to 3% by weight, relative to the total weight of the composition.

b) Alkyl(amido)ether Carboxylic Anionic Surfactants

The cosmetic composition according to the present invention also comprises one or more alkyl(amido)ether carboxylic anionic surfactants b).

The term "anionic surfactant" means a surfactant including, as ionic or ionizable groups, only anionic groups.

In the present description, a species is termed as being "anionic" when it bears at least one permanent negative charge or when it can be ionized as a negatively charged species, under the conditions of use of the composition of the invention (for example the medium or the pH) and not comprising any cationic charge.

The anionic surfactants are chosen from alkyl(amido) ether carboxylic (or carboxylate) surfactants. It is understood in the present description that the alkyl(amido)ether carboxylate anionic surfactants comprise at least one carboxylic or carboxylate function (—COOH or —$COO^-$) and may optionally also comprise one or more sulfate and/or sulfonate functions. Preferably, the alkyl(amido)ether carboxylate anionic surfactants do not comprise any sulfate and/or sulfonate functions.

They may be chosen from the following compounds: alkyl ether carboxylic acids, alkyl($C_6$-$C_{30}$ aryl) ether carboxylic acids, alkylamido ether carboxylic acids; and also the salts of these compounds; and mixtures thereof;

the alkyl and/or acyl groups of these compounds including from 6 to 30 carbon atoms, notably from 12 to 28, even better still from 14 to 24 or even from 16 to 22 carbon atoms; the aryl group preferably denoting a phenyl or benzyl group;

these compounds possibly being polyoxyalkylenated, notably polyoxyethylenated, and then preferably including from 1 to 50 ethylene oxide units and better still from 2 to 10 ethylene oxide units.

Preferentially, the anionic surfactants b) are chosen, alone or as a mixture, from:

- ($C_6$-$C_{24}$)alkyl ether carboxylates, and notably ($C_{12}$-$C_{20}$) alkyl ether carboxylates;
- polyoxyalkylenated ($C_6$-$C_{24}$)alkyl(amido) ether carboxylic acids, in particular those including from 2 to 50 ethylene oxide groups;

in particular in the form of alkali metal or alkaline-earth metal, ammonium or amino alcohol salts.

Among the above carboxylic surfactants, mention may also be made of polyoxyalkylenated alkyl(amido) ether carboxylic acids and salts thereof, in particular those including from 2 to 50 alkylene oxide and in particular ethylene oxide groups, such as the compounds sold by the company Kao under the Akypo names.

The polyoxyalkylenated alkyl(amido) ether carboxylic acids that may be used are preferably chosen from those of formula (II):

$$R_1—(OC_2H_4)_n—OCH_2COOA \quad \text{(II)}$$

in which:

- $R_1$ represents a linear or branched $C_6$-$C_{24}$ alkyl or alkenyl radical, a ($C_8$-$C_9$)alkylphenyl radical, a radical $R_2CONH—CH_2—CH_2—$ with $R_2$ denoting a linear or branched $C_9$-$C_{21}$ alkyl or alkenyl radical;

preferably, $R_1$ is a $C_8$-$C_{20}$ and preferably $C_8$-$C_{18}$ alkyl radical, and aryl preferably denotes phenyl,

- n is an integer or decimal number (mean value) ranging from 2 to 24 and preferably from 2 to 10,
- A denotes H, ammonium, Na, K, Li, Mg or a monoethanolamine or triethanolamine residue.

Use may also be made of mixtures of compounds of formula (II), in particular mixtures of compounds bearing different groups $R_1$.

The polyoxyalkylenated alkyl(amido) ether carboxylic acids that are particularly preferred are those of formula (II) in which:

- $R^1$ denotes a $C_{12}$-$C_{14}$ alkyl, cocoyl, oleyl, nonylphenyl or octylphenyl radical,
- A denotes a hydrogen or sodium atom, and
- n ranges from 2 to 20, preferably from 2 to 10.

Even more preferentially, use is made of the compounds of formula (II) in which $R_1$ denotes a $C_{12}$ alkyl radical, A denotes a hydrogen or sodium atom and n ranges from 2 to 10.

When the anionic surfactant is in salt form, said salt may be chosen from alkali metal salts, such as the sodium or potassium salt, ammonium salts, amine salts and in particular amino alcohol salts, and alkaline-earth metal salts, such as the magnesium salt.

Examples of amino alcohol salts that may be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

Among the commercial products that may preferably be used are the products sold by the company KAO under the names:

Akypo® NP 70 ($R_1$=nonylphenyl, n=7, A=H),
Akypo® NP 40 ($R_1$=nonylphenyl, n=4, A=H),
Akypo® OP 40 ($R_1$=octylphenyl, n=4, A=H),
Akypo® OP 80 ($R_1$=octylphenyl, n=8, A=H),
Akypo® OP 190 ($R_1$=octylphenyl, n=19, A=H),
Akypo® RLM 38 ($R_1$=($C_{12}$-$C_{14}$)alkyl, n=4, A=H),
Akypo® RLM 38 NV ($R_1$=($C_{12}$-$C_{14}$)alkyl, n=4, A=Na),
Akypo® RLM 45 CA ($R_1$=($C_{12}$-$C_{14}$)alkyl, n=4.5, A=H)
Akypo® RLM 45 NV ($R_1$=($C_{12}$-$C_{14}$)alkyl, n=4.5, A=Na),
Akypo® RLM 100 ($R_1$=($C_{12}$-$C_{14}$)alkyl, n=10, A=H),
Akypo® RLM 100 NV ($R_1$=($C_{12}$-$C_{14}$)alkyl, n=10, A=Na),
Akypo® RLM 130 ($R_1$=($C_{12}$-$C_{14}$)alkyl, n=13, A=H),
Akypo® RLM 160 NV ($R_1$=($C_{12}$-$C_{14}$)alkyl, n=16, A=Na), or by the company Sandoz under the names:

Sandopan DTC-Acid ($R_1$=($C_{13}$)alkyl, n=6, A=H),
Sandopan DTC ($R_1$=($C_{13}$)alkyl, n=6, A=Na),
Sandopan LS 24 ($R_1$=($C_{12}$-$C_{14}$)alkyl, n=12, A=Na),
Sandopan JA 36 ($R_1$=($C_{13}$)alkyl, n=18, A=H), and more particularly the products sold under the following names:

AKYPO® RLM 45 (INCI: Laureth-5 carboxylic acid),
AKYPO®RLM 100,
AKYPO® RLM 38.

Preferably, the alkyl(amido)ether carboxylic anionic surfactant(s) b) are chosen from alkyl ether carboxylic anionic surfactants.

The total content of the alkyl(amido)ether carboxylic anionic surfactant(s) b) advantageously ranges from 0.1% to 20% by weight, preferably from 0.5% to 10% by weight, more preferentially from 1% to 8% by weight, better still from 3% to 7% by weight, relative to the total weight of the composition.

Preferably, the total content of the alkyl ether carboxylic anionic surfactant(s) b) advantageously ranges from 0.1% to 20% by weight, preferably from 0.5% to 10% by weight, more preferentially from 1% to 8% by weight, better still from 3% to 7% by weight, relative to the total weight of the composition.

The composition according to the invention may optionally comprise one or more anionic surfactants other than the anionic surfactants b), but, preferably, said composition does not comprise any.

Advantageously, the weight ratio between the total content of the alkyl(amido)ether carboxylic anionic surfactant(s) b) and the total content of the cationic associative polymer(s) a) is less than or equal to 10, preferably between 1 and 10, more preferentially between 2 and 8.

Advantageously, the weight ratio between the total content of the alkyl ether carboxylic anionic surfactant(s) b) and the total content of the cationic associative polymer(s) a) is less than or equal to 10, preferably between 1 and 10, more preferentially between 2 and 8.

Advantageously, the weight ratio between the total content of the total anionic surfactant(s) and the total content of the cationic associative polymer(s) a) is less than or equal to 10, preferably between 1 and 10, more preferentially between 2 and 8.

c) Nonionic Surfactants

The cosmetic composition according to the invention also optionally comprises one or more nonionic surfactants c).

The nonionic surfactants that may be used are described, for example, in the *Handbook of Surfactants* by M. R. Porter, published by Blackie & Son (Glasgow and London), 1991, pages 116-178.

Examples of nonionic surfactants that may be mentioned include the following nonionic surfactants:

- oxyalkylenated ($C_8$-$C_{24}$)alkylphenols;
- saturated or unsaturated, linear or branched, oxyalkylenated or glycerolated $C_8$-$C_{40}$ alcohols;
- saturated or unsaturated, linear or branched, oxyalkylenated $C_8$ to $C_{30}$ fatty acid amides;
- esters of saturated or unsaturated, linear or branched, $C_8$-$C_{30}$ acids and of polyols or polyethylene glycols;
- preferably oxyethylenated esters of saturated or unsaturated, linear or branched, $C_8$ to $C_{30}$ acids and of sorbitol;
- esters of fatty acids and of sucrose;
- ($C_8$-$C_{30}$)alkyl(poly)glucosides, ($C_8$-$C_{30}$)alkenyl(poly)glucosides, which are optionally oxyalkylenated (0 to 10 oxyalkylene units) and comprise from 1 to 15 glucose units, ($C_8$-$C_{30}$)alkyl(poly)glucoside esters;
- saturated or unsaturated oxyethylenated plant oils;
- condensates of ethylene oxide and/or of propylene oxide;
- N-($C_8$-$C_{30}$)alkylglucamine and N-($C_8$-$C_{30}$)acylmethylglucamine derivatives;
- aldobionamides;
- amine oxides;
- oxyethylenated and/or oxypropylenated silicones;
- and mixtures thereof.

The oxyalkylene units are more particularly oxyethylene or oxypropylene units, or a combination thereof, preferably oxyethylene units.

The number of moles of ethylene oxide and/or of propylene oxide preferably ranges from 1 to 250, more particularly from 2 to 100 and better still from 2 to 50; the number of moles of glycerol notably ranges from 1 to 50 and better still from 1 to 10.

Advantageously, the nonionic surfactants according to the invention do not comprise any oxypropylene units.

As examples of glycerolated nonionic surfactants, use is preferably made of monoglycerolated or polyglycerolated $C_8$ to $C_{40}$ alcohols, comprising from 1 to 50 mol of glycerol and preferably from 1 to 10 mol of glycerol.

Among the glycerolated alcohols, it is more particularly preferred to use the $C_8/C_{10}$ alcohol containing 1 mol of glycerol, the $C_{10}/C_{12}$ alcohol containing 1 mol of glycerol and the Cu alcohol containing 1.5 mol of glycerol.

The nonionic surfactant(s) that may be used in the composition according to the invention are preferentially chosen from:

- oxyethylenated $C_8$ to $C_{40}$ alcohols comprising from 1 to 100 mol of ethylene oxide, preferably from 2 to 50 and more particularly from 2 to 40 mol of ethylene oxide;
- saturated or unsaturated oxyethylenated plant oils comprising from 1 to 100 and preferably from 2 to 50 mol of ethylene oxide;
- ($C_8$-$C_{30}$)alkyl(poly)glucosides, which are optionally oxyalkylenated (0 to 10 EO) and comprising 1 to 15 glucose units;
- monoglycerolated or polyglycerolated $C_8$ to $C_{40}$ alcohols, comprising from 1 to 50 mol of glycerol and preferably from 1 to 10 mol of glycerol;
- saturated or unsaturated, linear or branched, oxyalkylenated $C_8$ to $C_{30}$ fatty acid amides;
- esters of saturated or unsaturated, linear or branched, $C_8$-$C_{30}$ acids and of polyols or polyethylene glycols;
- and mixtures thereof.

Preferably, the nonionic surfactant(s) c) are chosen from saturated or unsaturated, linear or branched, oxyalkylenated or glycerolated, preferentially oxyethylenated, $C_8$ to $C_{40}$ alcohols, and mixtures thereof.

Preferably, the nonionic surfactant(s) c) are chosen from oxyethylenated $C_8$ to $C_{40}$, better still $C_{10}$-$C_{32}$, even better still $C_{10}$-$C_{20}$, or even $C_{12}$-$C_{18}$ alcohols comprising from 1 to 100 mol of ethylene oxide, preferably from 2 to 50 mol of ethylene oxide, more preferentially from 2 to 40 mol of ethylene oxide, better still from 2 to 20 mol of ethylene oxide.

More preferentially, the nonionic surfactant c) is oxyethylenated lauryl alcohol, preferably containing 4 mol of ethylene oxide.

When the composition comprises one or more nonionic surfactants c), advantageously, the total content of the nonionic surfactant(s) c) ranges from 0.01% to 10% by weight, preferably from 0.1% to 5% by weight, more preferentially from 0.5% to 2% by weight, relative to the total weight of the composition.

Preferably, the composition comprises one or more nonionic surfactant(s) c), more preferentially one or more nonionic surfactants c) chosen from oxyethylenated $C_8$ to $C_{40}$, better still $C_{10}$-$C_{32}$, even better still $C_{10}$-$C_{20}$, or even $C_{12}$-$C_{18}$ alcohols comprising from 1 to 100 mol of ethylene oxide, preferably from 2 to 50 mol of ethylene oxide, more preferentially from 2 to 40 mol of ethylene oxide.

d) Amphoteric or Zwitterionic Surfactants

The cosmetic composition according to the invention also comprises one or more amphoteric or zwitterionic surfactants d).

The amphoteric surfactants that may be used in the invention may be optionally quaternized secondary or tertiary aliphatic amine derivatives, in which the aliphatic group is a linear or branched chain including from 8 to 22 carbon atoms, said amine derivatives containing at least one anionic group, for instance a carboxylate, sulfonate, sulfate, phosphate or phosphonate group.

Mention may in particular be made of ($C_8$-$C_{20}$)alkylbetaines, sulfobetaines, ($C_8$-$C_{20}$)alkylsulfobetaines, ($C_8$-$C_{20}$)alkylamido($C_1$-$C_6$)alkylbetaines, such as cocoamidopropylbetaine, ($C_8$-$C_{20}$)alkylamido($C_1$-$C_6$)alkylsulfobetaines, and also mixtures thereof.

Among the derivatives of optionally quaternized secondary or tertiary aliphatic amines that may be used, mention may also be made of the products having the respective structures ($A_1$) and (A2) below:

$$R_a—CON(Z)CH_2—(CH_2)_m—N^+(R_b)(R_c)(CH_2COO_2) \quad (A1)$$

in which:

$R_a$ represents a $C_{10}$-$C_{30}$ alkyl or alkenyl group derived from an acid $R_a$—COOH preferably present in hydrolysed coconut kernel oil, or a heptyl, nonyl or undecyl group, $R_b$ represents a β-hydroxyethyl group, $R_c$ represents a carboxymethyl group;

m is equal to 0, 1 or 2, and

Z represents a hydrogen atom or a hydroxyethyl or carboxymethyl group;

$$R_{a'}—CON(Z)CH_2—(CH_2)_{m'}—N(B)(B') \quad (A2)$$

in which:

B represents —$CH_2CH_2OX'$, with X' representing —$CH_2$—COOH, $CH_2$—COOZ', —$CH_2CH_2$—COOH, —$CH_2CH_2$—COOZ', or a hydrogen atom, B' represents —$(CH_2)_z$-Y', with z=1 or 2, and Y' representing —COOH, —COOZ', —$CH_2$—CHOH—$SO_3H$ or $CH_2$—CHOH—$SO_3Z'$, m' is equal to 0, 1 or 2, Z represents a hydrogen atom or a hydroxyethyl or carboxymethyl group, Z' represents an ion derived from an alkali metal or alkaline-earth metal, such as sodium, potassium or magnesium; an ammonium ion; or an ion derived from an organic amine and notably from an amino alcohol, such as monoethanolamine, diethanolamine and triethanolamine, monoisopropanolamine, diisopropanolamine or triisopropanolamine, 2-amino-2-methyl-1-propanol, 2-amino-2-methyl-1,3-propanediol and tris(hydroxymethyl)aminomethane, and $R_{a'}$ represents a $C_{10}$-$C_{30}$ alkyl or alkenyl group of an acid $R_{a'}$COOH preferably present in hydrolysed linseed oil or coconut kernel oil, an alkyl group, notably a $C_{17}$ alkyl group, and its iso form, or an unsaturated $C_{17}$ group.

The compounds corresponding to formula (A2) are particularly preferred.

Among the compounds of formula (A2) for which X' represents a hydrogen atom, mention may be made of the compounds known under the (CTFA) names sodium cocoamphoacetate, sodium lauroamphoacetate, sodium caproamphoacetate and sodium capryloamphoacetate.

Other compounds of formula (A2) are known under the (CTFA) names disodium cocoamphodiacetate, disodium lauroamphodiacetate, disodium caproamphodiacetate, disodium capryloamphodiacetate, disodium cocoamphodipropionate, disodium lauroamphodipropionate, disodium caproamphodipropionate, disodium capryloamphodipropionate, lauroamphodipropionic acid and cocoamphodipropionic acid.

As examples of compounds of formula (A2), mention may be made of the cocoamphodiacetate sold by the company Rhodia under the trade name Miranol® C2M Concentrate, the sodium cocoamphoacetate sold under the trade name Miranol Ultra C 32 and the product sold by the company Chimex under the trade name Chimexane HA.

Use may also be made of the compounds of formula (A3):

$$R_{a''}—NH—CH(Y'')—(CH_2)_n—C(O)—NH—(CH_2)_{n'}—N(R_d)(R_e) \quad (A3)$$

in which:

$R_{a''}$ represents a $C_{10}$-$C_{30}$ alkyl or alkenyl group of an acid $R_{a''}$—C(O)OH, which is preferably present in hydrolysed linseed oil or coconut kernel oil;

Y'' represents the group —C(O)OH, —C(O)OZ'', —$CH_2$—CH(OH)—$SO_3H$ or the group $CH_2$—CH(OH)—$SO_3$—Z'', with Z'' representing a cation resulting from an alkali metal or alkaline-earth metal, such as sodium, an ammonium ion or an ion resulting from an organic amine;

$R_d$ and $R_e$, independently of each other, represent a $C_1$-$C_4$ alkyl or hydroxyalkyl radical; and n and n', independently of each other, denote an integer ranging from 1 to 3.

Among the compounds of formula (A3), mention may be made notably of the compound classified in the CTFA dictionary under the name sodium diethylaminopropyl cocoaspartamide and notably the compound sold by the company Chimex under the name Chimexane HB.

The amphoteric or zwitterionic surfactant(s) d) are advantageously chosen from ($C_8$-$C_{20}$)alkylbetaines, ($C_8$-$C_{20}$)alkylamido($C_3$-$C_8$)alkylbetaines, and mixtures thereof, and preferably from cocoylbetaine and cocamidopropylbetaine, and mixtures thereof.

The total content of the amphoteric or zwitterionic surfactant(s) d) advantageously ranges from 0.1% to 10% by weight, preferably from 0.25% to 8% by weight, more preferentially from 0.5% to 5% by weight, relative to the total weight of the composition.

In a preferred embodiment, the cosmetic composition according to the invention comprises:

a) one or more cationic associative polymers chosen from quaternized (poly)hydroxyethylcelluloses modified with groups including at least one fatty chain, b) one or more carboxylic anionic surfactants chosen from polyoxyalkylenated alkyl(amido)ether carboxylic acids and salts thereof, and mixtures thereof, more preferentially from polyoxyalkylenated ($C_6$-$C_{24}$)alkyl ether carboxylic acids and salts thereof, and mixtures thereof, c) one or more nonionic surfactants chosen from oxyethylenated $C_8$ to $C_{40}$ alcohols comprising from 1 to 100 mol of ethylene oxide, preferably from 2 to 50 mol of ethylene oxide and more preferentially from 2 to 40 mol of ethylene oxide, d) one or more amphoteric or zwitterionic surfactants chosen from ($C_8$-$C_{20}$)alkylbetaines, ($C_8$-$C_{20}$)alkylamido($C_3$-$C_8$)alkylbetaines, and mixtures thereof, and preferably from cocoylbetaine and cocamidopropylbetaine, and mixtures thereof, and e) optionally one or more silicones.

e) Silicones

The cosmetic composition according to the invention may also comprise one or more silicones e), which may be solid or liquid, and volatile or non-volatile.

The silicones e) are different from the cationic associative polymers a).

The silicones that may be used may be soluble or insoluble in the composition according to the invention; they may be in the form of oil, wax, resin or gum; silicone oils and gums are preferred.

Silicones are notably described in detail in Walter Noll's *Chemistry and Technology of Silicones* (1968), Academic Press.

The volatile silicones may be chosen from those with a boiling point of between 60° C. and 260° C. (at atmospheric pressure) and more particularly from:

i) cyclic polydialkylsiloxanes including from 3 to 7 and preferably 4 to 5 silicon atoms, such as octamethylcyclotetrasiloxane and decamethylcyclopentasiloxane.

Mention may be made of the products sold under the name Volatile Silicone 7207 by Union Carbide or Silbione 70045 V 2 by Rhodia, Volatile Silicone 7158 by Union Carbide or Silbione 70045 V 5 by Rhodia;

cyclocopolymers of the dimethylsiloxane/methylalkylsiloxane type having the chemical structure:

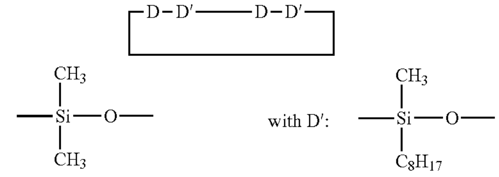

with D: with D′:

Mention may be made of Volatile Silicone FZ 3109 sold by the company Union Carbide;

mixtures of cyclic silicones with silicon-based organic compounds, such as the mixture of octamethylcyclotetrasiloxane and of tetratrimethylsilylpentaerythritol (50/50) and the mixture of octamethylcyclotetrasiloxane and of 1,1'-oxy(2,2,2',2',3,3'-hexatrimethylsilyloxy)bisneopentane;

ii) linear polydialkylsiloxanes containing 2 to 9 silicon atoms, which generally have a viscosity of less than or equal to $5\times10^{-6}$ $m^2/s$ at 25° C., such as decamethyltetrasiloxane.

Other silicones belonging to this category are described in the article published in Cosmetics and Toiletries, Vol. 91, January 76, pages 27-32, Todd & Byers *Volatile Silicone Fluids for Cosmetics*; mention may be made of the product sold under the name SH 200 by the company Toray Silicone.

Among the non-volatile silicones, mention may be made, alone or as a mixture, of polydialkylsiloxanes and notably polydimethylsiloxanes (PDMS), polydiarylsiloxanes, polyalkylarylsiloxanes, silicone gums and resins, and also organopolysiloxanes (or organomodified polysiloxanes, or alternatively organomodified silicones) which are polysiloxanes including in their structure one or more organofunctional groups, generally attached via a hydrocarbon-based group, and preferably chosen from aryl groups, amine groups, alkoxy groups and polyoxyethylene or polyoxypropylene groups.

The organomodified silicones may be polydiarylsiloxanes, notably polydiphenylsiloxanes, and polyalkylarylsiloxanes functionalized with the organofunctional groups mentioned previously. The polyalkylarylsiloxanes are particularly chosen from linear and/or branched polydimethyl/methylphenylsiloxanes and polydimethyl/diphenylsiloxanes.

Among the organomodified silicones, mention may be made of organopolysiloxanes including:

polyoxyethylene and/or polyoxypropylene groups optionally including $C_6$-$C_{24}$ alkyl groups, such as dimethicone copolyols, and notably those sold by the company Dow Corning under the name DC 1248 or the oils Silwet® L 722, L 7500, L 77 and L 711 from the company Union Carbide; or alternatively ($C_{12}$)alkylmethicone copolyols, and notably those sold by the company Dow Corning under the name Q2 5200;

substituted or unsubstituted amine groups, in particular $C_1$-$C_4$ aminoalkyl groups; mention may be made of the products sold under the names GP4 Silicone Fluid and GP7100 by the company Genesee, or under the names Q2-8220 and $DC_{929}$ or $DC_{939}$ by the company Dow Corning;

thiol groups, such as the products sold under the names GP 72 A and GP 71 from Genesee;

alkoxylated groups, such as the product sold under the name Silicone Copolymer F-755 by SWS Silicones and Abil Wax® 2428, 2434 and 2440 by the company Goldschmidt;

hydroxylated groups, for instance polyorganosiloxanes containing a hydroxyalkyl function;

acyloxyalkyl groups, such as the polyorganosiloxanes described in U.S. Pat. No. 4,957,732;

anionic groups of the carboxylic acid type, as described, for example, in EP 186 507, or of the alkylcarboxylic type, such as the product X-22-3701E from the company Shin-Etsu; or alternatively of the 2-hydroxyalkylsulfonate or 2-hydroxyalkylthiosulfate type, such as the products sold by the company Goldschmidt under the names Abil® 5201 and Abil® 5255;

hydroxyacylamino groups, such as the polyorganosiloxanes described in patent application EP 342 834; mention may be made, for example, of the product Q2-8413 from the company Dow Corning.

The silicones may also be chosen from polydialkylsiloxanes, among which mention may be made mainly of polydimethylsiloxanes bearing trimethylsilyl end groups. Among these polydialkylsiloxanes, mention may be made of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as $DC_{200,}$ with a viscosity of 60000 $mm^2/s$;

the Viscasil® oils from General Electric and certain oils of the SF series (SF 96, SF 18) from General Electric.

Mention may also be made of polydimethylsiloxanes bearing dimethylsilanol end groups, known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly($C_1$-$C_{20}$)dialkylsiloxanes.

Products that may be used more particularly in accordance with the invention are mixtures such as:

mixtures formed from a polydimethylsiloxane with a hydroxy-terminated chain, or dimethiconol (CTFA), and from a cyclic polydimethylsiloxane, also known as cyclomethicone (CTFA), such as the product Q2-1401 sold by the company Dow Corning.

The polyalkylarylsiloxanes are chosen particularly from linear and/or branched polydimethyl/methylphenylsiloxanes and polydimethyl/diphenylsiloxanes with a viscosity ranging from $1\times10^{-5}$ to $5\times10^{-2}$ $m^2/s$ at 25° C.

Among these polyalkylarylsiloxanes, mention may be made of the products sold under the following names:

the Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

The silicones that may be used may be amino silicones. The term "amino silicone" denotes any silicone including at least one primary, secondary or tertiary amine or a quaternary ammonium group.

The weight-average molecular masses of these amino silicones may be measured by gel permeation chromatography (GPC) at room temperature (25° C.), as polystyrene equivalent. The columns used are μ styragel columns. The eluent is THF and the flow rate is 1 ml/min. 200 μl of a 0.5% by weight solution of silicone in THF are injected. Detection is performed by refractometry and UV-metry.

Preferably, the amino silicone(s) that may be used in the context of the invention are chosen from:

a) the polysiloxanes corresponding to formula (A):

(A)

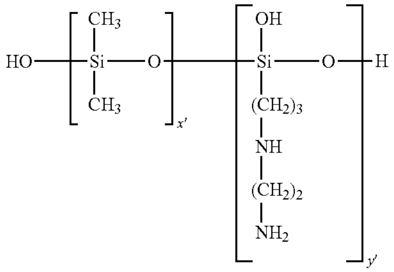

in which x' and y' are integers such that the weight-average molecular weight (Mw) is between 5000 and 500000 approximately;

b) the amino silicones corresponding to formula (B):

$R'_aG_{3-a}$-Si$(OSiG_2)_n$—$(OSiG_bR'_{2-b})_m$—O—$SiG_{3-a}$—$R'_a$ (B)

in which:

G, which may be identical or different, denotes a hydrogen atom or a group from among phenyl, OH, $C_1$-$C_8$ alkyl, for example methyl, or $C_1$-$C_8$ alkoxy, for example methoxy, a, which may be identical or different, denotes 0 or an integer from 1 to 3, in particular 0, b denotes 0 or 1, in particular 1, m and n are numbers such that the sum (n+m) ranges from 1 to 2000 and in particular from 50 to 150, n possibly denoting a number from 0 to 1999 and notably from 49 to 149, and m possibly denoting a number from 1 to 2000 and notably from 1 to 10;

R', which may be identical or different, denotes a monovalent radical of formula —$C_qH_{2q}L$ in which q is a number ranging from 2 to 8 and L is an optionally quaternized amino group chosen from the following groups:

—N(R")$_2$; —N$^+$(R")$_3$ A$^-$; —NR"-Q-N(R")$_2$ and —NR"—Q—N$^+$(R")$_3$ A$^-$, in which R", which may be identical or different, denotes hydrogen, phenyl, benzyl, or a saturated monovalent hydrocarbon-based radical, for example a $C_1$-$C_{20}$ alkyl radical; Q denotes a linear or branched group of formula $C_rH_{2r}$, r being an integer ranging from 2 to 6, preferably from 2 to 4; and $A^-$ represents a cosmetically acceptable anion, notably a halide such as fluoride, chloride, bromide or iodide.

Preferably, the amino silicones are chosen from the amino silicones of formula (B). Preferably, the amino silicones of formula (B) are chosen from the amino silicones corresponding to formulae (C), (D), (E), (F) and/or (G) below.

According to a first embodiment, the amino silicones corresponding to formula (B) are chosen from the silicones known as "trimethylsilyl amodimethicone" corresponding to formula (C):

(C)

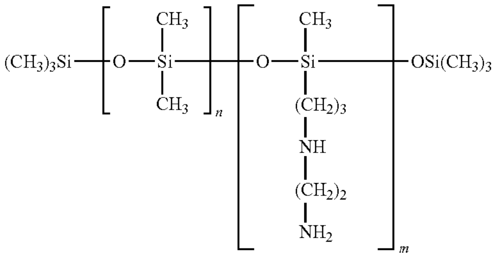

in which m and n are numbers such that the sum (n+m) ranges from 1 to 2000 and in particular from 50 to 150, n possibly denoting a number from 0 to 1999 and notably from 49 to 149, and m possibly denoting a number from 1 to 2000 and notably from 1 to 10.

According to a second embodiment, the amino silicones corresponding to formula (B) are chosen from the silicones of formula (D) below:

(D)

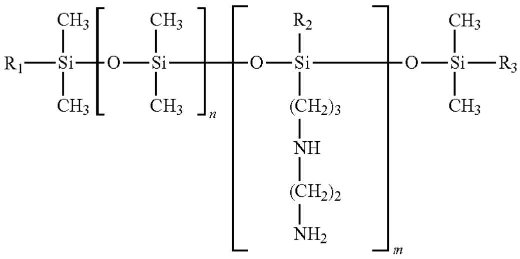

in which:

m and n are numbers such that the sum (n+m) ranges from 1 to 1000, in particular from 50 to 250 and more particularly from 100 to 200; n possibly denoting a number from 0 to 999, notably from 49 to 249 and more particularly from 125 to 175, and m possibly denoting a number from 1 to 1000, notably from 1 to 10 and more particularly from 1 to 5;

$R_1$, $R_2$ and $R_3$, which may be identical or different, represent a hydroxyl or $C_1$-$C_4$ alkoxy radical, at least one of the radicals $R_1$ to $R_3$ denoting an alkoxy radical.

Preferably, the alkoxy radical is a methoxy radical.

The hydroxy/alkoxy mole ratio preferably ranges from 0.2:1 to 0.4:1 and preferably from 0.25:1 to 0.35:1 and more particularly is equal to 0.3:1.

The weight-average molecular mass (Mw) of these silicones preferably ranges from 2000 to 1000000 and more particularly from 3500 to 200000.

According to a third embodiment, the amino silicones corresponding to formula (B) are chosen from the silicones of formula (E) below:

(E)

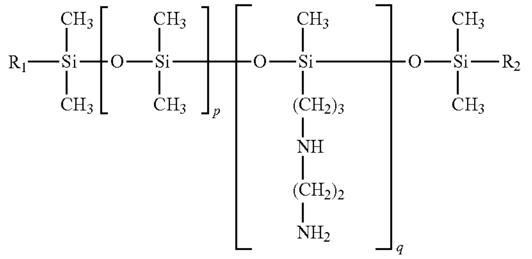

in which:

- p and q are numbers such that the sum (p+q) ranges from 1 to 1000, in particular from 50 to 350 and more particularly from 150 to 250; p possibly denoting a number from 0 to 999, notably from 49 to 349 and more particularly from 159 to 239, and q possibly denoting a number from 1 to 1000, notably from 1 to 10 and more particularly from 1 to 5;
- $R_1$ and $R_2$, which are different, represent a hydroxyl or $C_1$-$C_4$ alkoxy radical, at least one of the radicals $R_1$ or $R_2$ denoting an alkoxy radical.

Preferably, the alkoxy radical is a methoxy radical.

The hydroxy/alkoxy mole ratio generally ranges from 1:0.8 to 1:1.1 and preferably from 1:0.9 to 1:1 and more particularly is equal to 1:0.95.

The weight-average molecular mass (Mw) of the silicone preferably ranges from 2000 to 200000, even more particularly from 5000 to 100000 and more particularly from 10000 to 50000.

The commercial products comprising silicones of structure (D) or (E) may include in their composition one or more other amino silicones the structure of which is different from formula (D) or (E).

A product containing amino silicones of structure (D) is sold by the company Wacker under the name Belsil® ADM 652.

A product containing amino silicones of structure (E) is sold by Wacker under the name Fluid WR 1300®.

When these amino silicones are used, one particularly advantageous embodiment consists in using them in the form of an oil-in-water emulsion. The oil-in-water emulsion may comprise one or more surfactants. The surfactants may be of any nature but are preferably cationic and/or nonionic. The number-mean size of the silicone particles in the emulsion generally ranges from 3 nm to 500 nanometres. Preferably, notably as amino silicones of formula (E), use is made of microemulsions with a mean particle size ranging from 5 nm to 60 nanometres (limits included) and more particularly from 10 nm to 50 nanometres (limits included). Thus, use may be made according to the invention of the amino silicone microemulsions of formula (E) sold under the names Finish CT 96 E® or SLM 28020® by the company Wacker.

According to a fourth embodiment, the amino silicones corresponding to formula (B) are chosen from the silicones of formula (F) below:

(F)

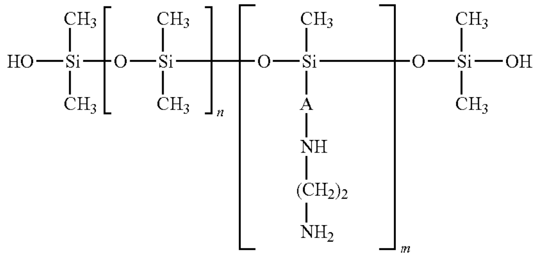

in which:

- m and n are numbers such that the sum (n+m) ranges from 1 to 2000 and in particular from 50 to 150, n possibly denoting a number from 0 to 1999 and notably from 49 to 149, and m possibly denoting a number from 1 to 2000 and notably from 1 to 10;
- A denotes a linear or branched alkylene radical containing from 4 to 8 carbon atoms and preferably 4 carbon atoms. This radical is preferably linear.

The weight-average molecular mass (Mw) of these amino silicones preferably ranges from 2000 to 1000000 and even more particularly from 3500 to 200000.

A silicone corresponding to this formula is, for example, the Xiameter MEM 8299 Emulsion from Dow Corning.

According to a fifth embodiment, the amino silicones corresponding to formula (B) are chosen from the silicones of formula (G) below:

(G)

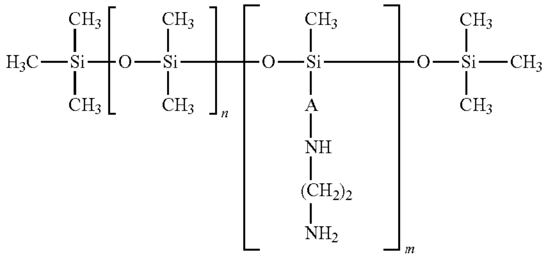

in which:

- m and n are numbers such that the sum (n+m) ranges from 1 to 2000 and in particular from 50 to 150, n possibly denoting a number from 0 to 1999 and notably from 49 to 149, and m possibly denoting a number from 1 to 2000 and notably from 1 to 10;
- A denotes a linear or branched alkylene radical containing from 4 to 8 carbon atoms and preferably 4 carbon atoms. This radical is preferably branched.

The weight-average molecular mass (Mw) of these amino silicones preferably ranges from 500 to 1000000 and even more particularly from 1000 to 200000.

A silicone corresponding to this formula is, for example, $DC_2$-8566 Amino Fluid from Dow Corning;

c) the amino silicones corresponding to formula (H):

(H)

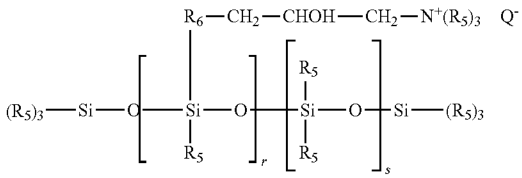

in which:

$R_5$ represents a monovalent hydrocarbon-based radical containing from 1 to carbon atoms, and in particular a $C_1$-$C_{18}$ alkyl or $C_2$-$C_{18}$ alkenyl, for example methyl, radical;

$R_6$ represents a divalent hydrocarbon-based radical, notably a $C_1$-$C_{18}$ alkylene radical or a divalent $C_1$-$C_{18}$, for example $C_1$-$C_8$, alkyleneoxy radical linked to the Si via an SiC bond;

$Q^-$ is an anion such as a halide ion, notably chloride, or an organic acid salt, notably acetate;

r represents a mean statistical value ranging from 2 to 20 and in particular from 2 to 8;

s represents a mean statistical value ranging from 20 to 200 and in particular from 20 to 50.

Such amino silicones are notably described in patent U.S. Pat. No. 4,185,087.

d) the quaternary ammonium silicones of formula (I):

(I)

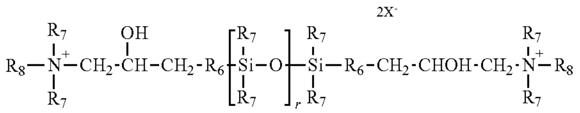

in which:

$R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring comprising 5 or 6 carbon atoms, for example methyl;

$R_6$ represents a divalent hydrocarbon-based radical, notably a $C_1$-$C_{18}$ alkylene radical or a divalent $C_1$-$C_{18}$, for example $C_1$-$C_8$, alkyleneoxy radical linked to the Si via an SiC bond;

$R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a radical $—R_6—NHCOR_7$;

$X^-$ is an anion such as a halide ion, notably chloride, or an organic acid salt, notably acetate;

r represents a mean statistical value ranging from 2 to 200 and in particular from 5 to 100.

These silicones are described, for example, in patent application EP-A 0 530 974;

e) the amino silicones of formula (J):

(J)

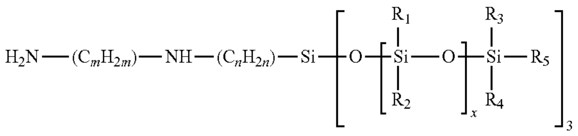

in which:

$R_1$, $R_2$, $R_3$ and $R_4$, which may be identical or different, denote a $C_1$-$C_4$ alkyl radical or a phenyl group, $R_5$ denotes a $C_1$-$C_4$ alkyl radical or a hydroxyl group, n is an integer ranging from 1 to 5, m is an integer ranging from 1 to 5, and x is chosen such that the amine number ranges from 0.01 to 1 meq/g;

f) multiblock polyoxyalkylenated amino silicones, of the type $(AB)_n$, A being a polysiloxane block and B being a polyoxyalkylenated block including at least one amine group.

Said silicones are preferably formed from repeating units having the following general formulae:

$$[—(SiMe_2O)_xSiMe_2—R—N(R'')—R'—O(C_2H_4O)_a(C_3H_6O)_b—R'—N(H)—R—]$$

or alternatively $$[—(SiMe_2O)_xSiMe_2—R—N(R'')\text{-}R'—O(C_2H_4O)_a(C_3H_6O)_b\text{-}]$$

in which:

a is an integer greater than or equal to 1, preferably ranging from 5 to 200 and more particularly ranging from 10 to 100;

b is an integer between 0 and 200, preferably ranging from 4 to 100 and more particularly between 5 and 30;

x is an integer ranging from 1 to 10000 and more particularly from 10 to 5000;

R" is a hydrogen atom or a methyl;

R, which may be identical or different, represent a linear or branched divalent $C_2$-$C_{12}$ hydrocarbon-based radical, optionally including one or more heteroatoms such as oxygen; preferably, R denotes an ethylene radical, a linear or branched propylene radical, a linear or branched butylene radical or a $CH_2CH_2CH_2OCH_2CH(OH)CH_2—$ radical; preferentially, R denotes a $CH_2CH_2CH_2OCH_2CH(OH)CH_2—$ radical;

R', which may be identical or different, represent a linear or branched divalent $C_2$-$C_{12}$ hydrocarbon-based radical, optionally including one or more heteroatoms such as oxygen; preferably, R' denotes an ethylene radical, a linear or branched propylene radical, a linear or branched butylene radical or a radical $CH_2CH_2CH_2OCH_2CH(OH)CH_2—$; preferentially, R' denotes $—CH(CH_3)—CH_2—$.

The siloxane blocks preferably represent between 50 mol % and 95 mol % of the total weight of the silicone, more particularly from 70 mol % to 85 mol %.

The amine content is preferably between 0.02 and 0.5 meq/g of copolymer in a 30% solution in dipropylene glycol, more particularly between 0.05 and 0.2.

The weight-average molecular mass (Mw) of the silicone is preferably between 5000 and 1000000 and more particularly between 10000 and 200000.

Mention may notably be made of the silicones sold under the name Silsoft A-843 or Silsoft A+ by Momentive.

g) and mixtures thereof.

Preferably, the amino silicones are chosen from multi-block polyoxyalkylenated amino silicones.

The silicone(s) e) are preferably chosen from polydialkylsiloxanes, organomodified silicones, amino silicones and mixtures thereof, more preferentially from polydialkylsiloxanes, amino silicones and mixtures thereof.

When the composition comprises one or more silicones, the total content of the silicone(s) e) preferably ranges from 0.01% to 10% by weight, preferably from 0.05% to 5% by weight and more preferentially from 0.1% to 2% by weight relative to the total weight of the composition.

Preferably, the composition according to the invention is silicone-free.

Additives

The cosmetic composition according to the present invention may also optionally comprise one or more additives, other than the compounds of the invention and among which mention may be made of cationic and anionic surfactants, and mixtures thereof, different from the surfactants of the invention, cationic, anionic, nonionic or amphoteric polymers, or mixtures thereof, different from the polymers of the invention, antidandruff agents, anti-seborrhoea agents, vitamins and provitamins including panthenol, sunscreens, sequestrants, plasticizers, solubilizers, acidifying agents, alkaline agents, thickeners, antioxidants, hydroxy acids, fragrances and preserving agents.

Needless to say, a person skilled in the art will take care to select this or these optional additional compounds such that the advantageous properties intrinsically associated with the composition according to the invention are not, or are not substantially, adversely affected by the envisaged addition(s).

The above additives may generally be present in an amount, for each of them, of between 0 and 20% by weight relative to the total weight of the composition.

According to a preferred embodiment, the composition is transparent.

For the purposes of the present invention, the term "transparent composition" means that the composition has a turbidity of less than 100 NTU, preferably less than or equal to 50 NTU, or even less than or equal to 20 NTU, and better still less than or equal to 10 NTU.

The transparency of the composition according to the invention may be characterized by turbidimetry (in NTU units, these being nephelometric units for measuring turbidity). The turbidity measurements may be performed with a 2100P model turbidimeter from the Hach Company, at room temperature (25° C.) and atmospheric pressure.

According to another embodiment, the composition according to the invention is opaque. In this embodiment, the use of a pH agent makes it possible to form an opaque composition.

A subject of the present invention is also a cosmetic process for treating keratin fibres, in particular human keratin fibres such as the hair, comprising the application to said keratin fibres of a composition as defined previously.

The cosmetic composition according to the invention may be applied to dry or wet keratin fibres, preferably wet keratin fibres, that have optionally been washed with shampoo.

Advantageously, the composition is applied to the keratin fibres for a leave-on time ranging from 1 minute to 20 minutes.

The keratin fibres are preferably rinsed after application of said cosmetic composition.

A subject of the invention is also the use of the cosmetic composition as defined previously for conditioning keratin fibres, in particular human keratin fibres such as the hair.

In a particular embodiment of the invention, the composition according to the invention is used for caring for and/or conditioning keratin fibres, in particular human keratin fibres such as the hair, notably for disentangling, smoothness and suppleness.

The examples that follow serve to illustrate the invention without, however, being limiting in nature.

EXAMPLES

In the examples that follow, all the amounts are indicated as weight percentages of active material relative to the total weight of the composition.

Example 1

Compositions A, B and C were prepared from the ingredients whose contents are indicated in the table below:

TABLE 1

| | Composition A | Composition B | Composition C |
|---|---|---|---|
| Polyquaternium-67 | 0.8 | 0.9 | 1.1 |
| Laureth-4 | 1.8 | 0.37 | 1.4 |
| Ethoxylated (PEG-40) and hydrogenated castor oil | — | 1.2 | — |
| Laureth-5 carboxylic acid | 2.2 | 5.5 | 5.3 |
| Cocamidopropyl betaine | 1.9 | 2.6 | 2 |
| NaCl | 1.1 | 0.7 | — |
| Water | qs 100 | qs 100 | qs 100 |

Compositions A, B and C may be used as hair conditioner.

When applied to sensitized hair (SA20), it is observed that they afford disentangling; they leave the hair supple and smooth to touch.

Composition B was compared with a commercial hair conditioner, on sensitized hair washed beforehand with a commercial shampoo and rinsed:

4 g of test composition are applied per half-head, and the hair is rinsed and then dried; six experts evaluate the hair under blind conditions.

The following results are obtained:

composition B according to the invention affords novel galenics more at the surface by virtue of its foaming aspect, facilitating the distribution, with faster rinsing;

on wet hair: hair treated with composition B according to the invention has a smoother feel with a coating that is more present, facilitating disentangling;

on dry hair: hair treated with the composition of the invention is visually smoother; however, slightly less supple fibres are observed, the hair is less disentangled and not as light.

The composition according to the invention thus affords very good strength, leaving an impression of a head of hair that is more dense and less supple.

Example 2

Compositions D (invention) and E (comparative) were prepared from the ingredients whose contents are indicated in the table below:

TABLE 2

| | Composition D (invention) | Composition E (comparative) |
|---|---|---|
| Laureth-5 carboxylic acid | 6.3 | 6.3 |
| Cocamidopropyl betaine | 3.8 | 3.8 |
| Laureth-4 | 5 | 5 |
| 3-Aminopropyltriethoxysilane | 2 | 2 |
| Polyquaternium-67 | 1.8 | — |
| Polyquaternium-6 | — | 1.8 |
| NaCl | 1.2 | 1.2 |
| Lactic acid | 0.72 | 0.72 |
| Preservatives | qs | qs |
| pH agents | qs pH5 | qs pH5 |
| Water | qs 100 | qs 100 |
| Weight ratio Laureth-5 carboxylic acid/Polyquaternium-67 | 3.5 | — |

a) Protocol

Compositions D and E are applied to locks of hair at a rate of 0.4 grams per gram of hair, distributed in a homogeneous and standardized manner, from the roots to the ends (by kneading the strands for 15 seconds).

After a pause of 5 minutes, the hair is rinsed with water at 35° C. (flow rate 300l/h) for 10 seconds, and wrung out.

The hair is then dried for 15 minutes in an oven at 60° C.

Then the visual aspect of both compositions, their quality of use (rinseability) and cosmetic properties (lightness) are evaluated.

b) Visual Aspect

Comparative composition E presents a cloudy and opaque aspect, whereas composition D according to the invention is limpid and opalescent.

c) Quality of use: Rinseability

Each lock is placed vertically under a water tap (water temperature of 35° C.) with a flow rate of 2 litres/minutes, for 5 seconds. This corresponds to a $1^{st}$ passage. This protocol is repeated 14 times.

After 15 rinses, the disappearance of the product is evaluated visually and tactilely.

Fibres treated with the comparative composition E have a very greasy and loaded touch and appearance, Whereas, the fibres treated with composition D according to the invention have a clean touch.

The composition D according to invention has a significantly improved rinseability compared to the comparative composition E. Thus, the composition according to invention D makes it possible to reduce the rinsing time and the quantity of water necessary for optimal rinsing in comparison with the comparative composition.

d) Cosmetic property: lightness (fibres not weighed down)

The lightness of the hair was assessed visually and tactilely on dry hair.

The hair treated with composition D according to the invention is well individualized and appears flowing, without bundles, in contrast to the hair treated with comparative composition E.

The composition D according to the invention has improved the lightness of the hair, the fibres are significantly less heavy than when treated with the comparative composition E.

The invention claimed is:

1. A cosmetic composition comprising:

a) one or more cationic associative polymers comprising in its structure at least one hydrophobic group corresponding to a radical or polymer with a saturated or unsaturated, linear or branched hydrocarbon-based chain, comprising at least 8 carbon atoms in a total content ranging from 0.01% to 10% by weight, relative to the total weight of the composition, b) one or more alkylether carboxylic anionic surfactants in a total content ranging from 0.1% to 20% by weight, relative to the total weight of the composition, (c) one or more nonionic surfactants chosen from oxyethylenated $C_{12}$-$C_{18}$ alcohols comprising from 2 to 20 mol of ethylene oxide in a total content ranging from 0.01% to 10% by weight, relative to the total weight of the composition, (d) one or more amphoteric or zwitterionic surfactants chosen from (C8- C20) alkylamido (C1-C6) alkylbetaines in a total content ranging from 0.1% to 10% by weight, relative to the total weight of the composition, and (e) optionally one or more silicones, wherein the weight ratio between the total content of the alkylether carboxylic anionic surfactant(s) b) and the total content of the cationic associative polymer(s) a) is between 2 and 10.

2. The composition according to claim 1, wherein the cationic associative polymer(s) are chosen from quaternized (poly) hydroxyethylcelluloses modified with groups including at least one alkyl group containing at least 10 carbon atoms.

3. The composition according to claim 1, wherein the cationic associative polymer(s) a) are present in a total content ranging from 0.05% to 5% by weight, relative to the total weight of the composition.

4. The composition according to claim 1, wherein the alkylether carboxylic anionic surfactants b) are chosen from ($C_{12}$-$C_{20}$) alkyl ether carboxylates comprising from 2 to 50 ethylene oxide groups.

5. The composition according to claim 1, wherein the alkylamidoether carboxylic anionic surfactants or alkylether carboxylic anionic surfactants b) are present in a total content ranging from 0.5% to 10% by weight, relative to the total weight of the composition.

6. The composition according to the claim 1, wherein it further comprises nonionic surfactant(s) c) chosen from oxyalkylenated ($C_8$-$C_{24}$) alkylphenols; saturated or unsaturated, linear or branched, glycerolated $C_8$ to $C_{40}$ alcohols; saturated or unsaturated, linear or branched, oxyalkylenated $C_8$ to C30 fatty acid amides; esters of saturated or unsaturated, linear or branched $C_8$ to C30 acids and of polyols or of polyethylene glycols; esters, which are optionally oxyethylenated, of saturated or unsaturated, linear or branched $C_8$ to C30 acids and of sorbitol; fatty acid esters of sucrose; C8-C30 alkenyl (poly) glucosides, C8-C30 alkenyl (poly) glucosides, which are optionally oxyalkylenated (0 to 10 oxyalkylene units) and comprising from 1 to 15 glucose units, C8-C30 alkyl (poly) glucoside esters; oxyethylenated, saturated or unsaturated plant oils; condensates of ethylene oxide and/or of propylene oxide; N-(C8-C30) alkylglucamine and N-(C8-C30) acylmethylglucamine derivatives; aldobionamides; amine oxides; oxyethylenated and/or oxypropylenated silicones; and mixtures thereof.

7. The composition according to claim 1, wherein the nonionic surfactant(s) c) are present in a total content ranging from 0.01% to 5% by weight, relative to the total weight of the composition.

8. The composition according to claim 1, wherein the amphoteric or zwitterionic surfactant(s) d) are present in a total content ranging from 0.01% to 10% by weight, relative to the total weight of the composition.

9. The composition according to claim 1, wherein the silicone(s) e) are present and are chosen from polydialkylsiloxanes, organomodified silicones, amino silicones and mixtures thereof.

10. The composition according to claim 1, wherein the silicone(s) e) are present in a total content ranging from 0.01% to 10% by weight, relative to the total weight of the composition.

11. The composition according to claim 1, wherein the hydrophobic group of the cationic associative polymer(s) has from 10 to 22 carbon atoms.

12. A cosmetic process for treating keratin fibers, comprising applying the composition of claim 1 to keratin fibers.

13. The cosmetic process of claim 12, wherein the keratin fibers are human keratin fibers.

14. The cosmetic process of claim 12, wherein the keratin fibers are hair.

15. The cosmetic process of claim 13, wherein the keratin fibers are hair.

* * * * *